(12) United States Patent
Sapienza et al.

(10) Patent No.: US 8,906,251 B2
(45) Date of Patent: *Dec. 9, 2014

(54) ENVIRONMENTALLY BENIGN ANTI-ICING OR DEICING FLUIDS

(71) Applicant: MLI Associates, LLC, Colombus, OH (US)

(72) Inventors: Richard Sapienza, Greenfield, OH (US); Axel Johnson, North Babylon, NY (US); William Ricks, Galena, OH (US)

(73) Assignee: MLI Associates, L.L.C., Colombus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/738,286

(22) Filed: Jan. 10, 2013

(65) Prior Publication Data

US 2013/0126779 A1     May 23, 2013

Related U.S. Application Data

(63) Continuation of application No. 13/341,000, filed on Dec. 30, 2011, now Pat. No. 8,377,328, which is a continuation of application No. 12/944,265, filed on Nov. 11, 2010, now Pat. No. 8,313,667, which is a continuation-in-part of application No. 11/901,301, filed on Sep. 17, 2007, now Pat. No. 7,854,856, which is a continuation of application No. 11/114,939, filed on Apr. 26, 2005, now Pat. No. 7,270,768, which is a continuation-in-part of application No. 10/668,674, filed on Sep. 23, 2003, now Pat. No. 6,890,451.

(51) Int. Cl.
*C09K 3/18*     (2006.01)
*C09K 5/20*     (2006.01)
*C07C 31/22*     (2006.01)

(52) U.S. Cl.
CPC . *C09K 5/20* (2013.01); *G09K 3/185* (2013.01); *C07C 31/225* (2013.01); *C09K 3/18* (2013.01)
USPC .................. 252/70; 106/13; 252/71; 252/73; 252/79

(58) Field of Classification Search
CPC ............ C09K 3/18; C09K 3/185; C09K 5/20; C07C 31/225
USPC .............................. 252/70, 71, 73, 79; 106/13
See application file for complete search history.

(56) References Cited

U.S. PATENT DOCUMENTS 8,377,328 B2 *   2/2013   Sapienza et al. ................ 252/70

* cited by examiner

*Primary Examiner* — Anthony J Green
(74) *Attorney, Agent, or Firm* — Locke Lord LLP; Alan B. Clement; Peter J. Fallon

(57) ABSTRACT

Deicing compositions comprised of glycerol-containing byproducts of triglyceride processing processes are disclosed.

5 Claims, No Drawings

ENVIRONMENTALLY BENIGN ANTI-ICING OR DEICING FLUIDS

CROSS REFERENCE TO RELATED APPLICATION

This application is a continuation application of application Ser. No. 13/341,000 filed on Dec. 30, 2011, now U.S. Pat. No. 8,377,328 and issued Feb. 19, 2013, which is a continuation application of application Ser. No. 12/944,265 filed Nov. 11, 2010, now U.S. Pat. No. 8,313,667 and issued Nov. 20, 2013, which is a continuation-in-part of application Ser. No. 11/901,301, filed Sep. 17, 2007 now U.S. Pat. No. 7,854,856 and issued Dec. 21, 2010, which is a continuation of application Ser. No. 11/114,939, filed Apr. 26, 2005, now U.S. Pat. No. 7,270,768, and issued Sep. 18, 2007, which in turn is a continuation-in-part of application Ser. No. 10/668,674, filed Sep. 23, 2003, now U.S. Pat. No. 6,890,451, which issued May 10, 2005.

FIELD OF THE INVENTION

The present invention relates to deicing fluid compositions and methods for deicing surfaces and for preventing ice formation (anti-icing) on surfaces or within fluids. More particularly the present invention relates to deicing/anti-icing fluid compositions comprising components obtained as glycerol-containing by-products of processing triglycerides for the purpose of manufacturing products such as biodiesel.

BACKGROUND OF THE INVENTION

Freezing point lowering compositions are in widespread use for a variety of purposes, especially to reduce the freezing point of an aqueous system so that ice cannot be formed or to melt formed ice. Generally, freezing point lowering compositions depend for their effectiveness upon the molar freezing point lowering effect, the number of ionic species that are made available and the degree to which the compositions can be dispersed in the liquid phase in which the formation of ice is to be precluded and/or ice is to be melted.

The most pervasive of the commonly used products for deicing are common salt, calcium chloride, magnesium chloride and urea, with common salt (sodium chloride) being the least expensive and most commonly used. Common salt widely is used to melt ice on road surfaces and the like. In this manner the salt forms a solution with the available liquid in contact with the ice and thereby forms a solution with a lower freezing point than the ice itself so that the ice is melted. Chloride salts, however, suffer from relatively severe drawbacks, such as the harmful effects on surrounding vegetation by preventing water absorption in the root systems, the corrosive effects on animal skin such as the feet of animals, clothing, roadways and motor vehicles, and the deleterious effects on surface and ground water. Thus, any new method of deicing or new deicing composition that can reduce the amount of chloride salts, or eliminate chloride salts entirely, would solve a long felt need in the art.

Other inorganic salts also are known to be useful as freezing point lowering agents such as, potassium phosphates, sodium phosphates, ammonium phosphates, ammonium nitrates, alkaline earth nitrates, magnesium nitrate, ammonium sulfate and alkali sulfates.

Another drawback of certain prior art deicing fluids is their high chemical and biological oxygen demands, which make them environmentally unfavorable. The glycols are exemplary of deicing fluids that particularly suffer from this type of environmental drawback. Thus, any new method of deicing or new deicing composition that can reduce the chemical or short term biological oxygen demands also would solve a long felt need in the art.

Typical solutions of low freezing point deicing and anti-icing agents include chloride salt brines, ethylene glycol and propylene glycol solutions. The use of chloride brines in anti-icing compounds can reduce, although not eliminate, the impacts of chlorides when applied as solids for deicing. Brines and glycol solutions also are employed as components of fluids used to transfer heat in applications where the fluid may be exposed to temperatures below the normal freezing point of water. Ethylene glycol solutions are well known for use as coolants for automobiles and the like in regions where the temperature may fall below the normal freezing point of water. Ethylene and propylene glycols are used in relatively large quantities at major airports in northern climates in order to keep air traffic flowing during inclement weather. The fluids generally are applied to the wings, fuselage and tail of aircraft and in some instances to the runways to remove ice. However, as mentioned above, these glycol compounds likewise have environmental drawbacks and can be detrimental to aquatic life and to sewage treatment processes.

Other prior art deicing fluids, such as alcohols, have toxic effects and high volatility particularly in the low molecular weight range. Further, some of these may be the cause of offensive smell and fire danger. Furthermore, mono- and polyhydric alcohols oxidize in the presence of atmospheric oxygen to form acids, which can increase corrosion of materials.

Due to the problems associated with deicing agents as described above there have been attempts to discover even more deicing agents. For, example, Kaes, U.S. Pat. No. 4,448,702, discloses the use of a freezing-point lowering composition and method that calls for the addition of a water soluble salt of at least one dicarboxylic acid having at least three carbon atoms, such as a sodium, potassium, ammonium or organoamine salt of adipic, glutaric, succinic or malonic acid.

Peel, U.S. Pat. No. 4,746,449, teaches the preparation of a deicing agent comprising 12-75% acetate salts, trace-36% carbonate salts, 1-24% formate salts and 1-32% pseudolactate salts that is prepared from a pulp mill black liquor by fractionating the black liquor into a low molecular weight fraction and concentrating the collected low molecular weight fraction to produce the deicing agent.

U.S. Pat. No. 4,960,531 teaches that small amounts of methyl glucosides, i.e., less than 10%, can be employed as a trigger to conventional salt deicers.

Back et al., U.S. Pat. No. 5,993,684, teach the use of polyhydric alcohols including glycerol in anti-icing or deicing applications, but does not teach the use of by-product streams from triglyceride processing comprising glycerol. Further, Back et al. teach against the inclusion of potassium and halide salts or the use of glycol in formulations.

Parks et al., U.S. Pat. No. 4,501,775, teach the use of low concentrations of polyhydroxyalkanes including glycerol, for the specific purpose of application to coal and mineral ores to insure that any ice formed is physically weak and will not deter the unloading of the coal or mineral ores. Further, Parks et al. do not teach the use of by-product streams from triglyceride processing comprising glycerol.

Roe, U.S. Pat. No. 4,426,409, teaches the use of polyhydric alcohols, including glycerol, in formulations for the purpose, as in Parks et al. above, of reducing the cohesive strength of particles when frozen. Further, Roe does not teach the use of by-product steams from triglyceride processing comprising glycerol.

Special mention is also made of the Sapienza patents, e.g., U.S. Pat. Nos. 5,876,621, 5,980,774, 6,129,857 and 6,506,318, which disclose especially useful deicing and anti-icing compositions.

Mention also is made of a number of other patents that employ industrial process streams in preparing deicing and/or anti-icing compositions. Examples of such patents are Bloomer, U.S. Pat. No. 6,080,330 (desugared sugar beet molasses); Toth et al., U.S. Pat. No. 4,676,918 (alcohol distilling waste); Janke et al., U.S. Pat. No. 5,709,812 (whey); Janke et al., U.S. Pat. No. 5,709,813 (vintner's condensed solubles); Janke et al., U.S. Pat. No. 5,635,101 (corn wet milling process by-products); Bytnar, U.S. Pat. No. 6,468,442 (corn syrup); and Hartley et al., U.S. Pat. No. 6,299,793 (corn syrup).

However, there still exists in the art a need for further improved deicing and/or anti-icing compositions and methods that are environmentally benign and relatively inexpensive to obtain. Preferably, these new and improved compositions are free from or significantly reduce the use of inorganic salts, are more environmentally benign and are prepared from relatively inexpensive raw materials while still possessing desirable freezing point depression properties. Likewise, there also exists a need in the art for new deicing and/or anti-icing agents that can be used in combination with prior art deicing agents, such as inorganic salts or glycols, to substantially reduce the amount of inorganic salts or glycols needed to accomplish the deicing/anti-icing objectives and, thereby, concomitantly reduce the environmental effects of the salts and/or glycols. Surprisingly, it has been found that compositions disclosed herein meet these needs while facilitating by-product disposition from production of soaps, fatty acids and bio-diesel. Production of biodiesel is an important strategy to reduce dependence on fossil hydrocarbons for transportation fuel and providing a means for achieving economic value from the by-product stream is an important element in achieving reasonable production economics.

SUMMARY OF THE INVENTION

The present inventors have found that excellent deicing compositions can be obtained from the by-product of reactions with triglycerides to produce monoesters for application to engine fuel commonly known as biodiesel. Triglycerides, the principal components of animal fats and of vegetable oils, are esters of glycerol (glycerine), a trihydric alcohol, with fatty acids of varying molecular weight. The triglyceride reactions of interest involve the use of monoalcohols and include, but are not limited to, (1) hydrolysis to produce fatty acids for subsequent reaction with monoalcohols to produce monoesters for use as biodiesel. and (2) transesterification reactions with monoalcohols to produce monoesters that can be employed as diesel engine fuel (biodiesel). Production of biodiesel, is of growing importance as part of the efforts to reduce dependence on fossil fuels, and one impediment in this field is finding a profitable use for the glycerol containing by-product of the reaction. It is therefore a preferred embodiment of the present invention to provide deicing and/or anti-icing compositions comprising by-products of reactions with triglycerides to produce monoesters, said by-products comprising glycerol.

In a further preferred embodiment of the present invention, the triglyceride processing by-product deicing and/or anti-icing composition is combined with an effective freezing point lowering amount of (a) a hydroxyl-containing organic compound selected from the group consisting of hydrocarbyl aldosides; sorbitol and other hydrogenation products of sugars, monosaccharides, maltodextrins and sucrose; maltitol; glycols; monosaccharides and mixtures thereof, and/or (b) an organic acid salt selected from the group consisting of a carbonic acid salt, a carboxylic acid salt, a hydroxycarboxylic acid salt, a dicarboxylic acid salt and mixtures thereof.

The present invention still further provides a method for reducing the amount of inorganic salt necessary to achieve effective deicing and/or anti-icing, comprising adding to the inorganic salt, an effective freezing point reducing amount of the triglyceride processing by-product deicing and/or anti-icing composition alone, or in combination with an effective freezing point lowering amount of (a) a hydroxyl-containing organic compound selected from the group consisting of hydrocarbyl aldosides; sorbitol and other hydrogenation products of sugars, monosaccharides, maltodextrins and sucrose; maltitol; glycols; monosaccharides and mixtures thereof, and/or (b) an organic acid salt selected from the group consisting of a carbonic acid salt, a carboxylic acid salt, a hydroxycarboxylic acid salt, a dicarboxylic acid salt and mixtures thereof.

The compositions of the present invention further may comprise a variety of other materials to enhance the deicing and anti-icing performance, such as, but not limited to, coarse solids to improve vehicle traction, corrosion inhibitors to prevent or reduce vehicular and infrastructure corrosion and buffers to control the pH of the compositions.

The compositions and methods of the present invention can be applied to a wide variety of surfaces, including both metallic and non-metallic surfaces of aircraft, which prevents icing, removes frozen water from the surface and prevents its reformation. The invention provides for a deicing composition that can be used on airport runways, bridges, streets, other structures including power lines and industrial equipment such as the decks and exposed superstructure of ships, conveyor systems, storage facilities, support systems and the like. Further, the compositions can be used in heat transfer applications such as, but not limited to, vehicular radiator systems such as automobile radiator coolants, air conditioning systems such as air conditioner fluids and systems for transferring process heat and systems for recovery of heat from process or power generating systems such as process heat transfer fluids, and in other applications in which it is vital or desired to maintain a liquid in the unfrozen state, e.g., as in a fire extinguisher, hydraulic fluids, lavatory fluids or in well drilling fluids, such as those used in drilling for oil and gas. Additionally, the present invention provides for an anti-icing composition that can be applied to a surface, such as bridges, prior to the onset of icing conditions in order to prevent icing from occurring. Other exemplary surfaces on which the deicing and/or anti-icing compositions of the present invention may be applied include pedestrian walkways, vehicular roadways, highways, bridges, parking facilities, aircraft surfaces such as wings, fuselage and tail surface, airport runways and taxiways, a deck or superstructure of a ship and weather exposed industrial equipment such as conveyor systems, storage facilities, support systems and lines for transmission of electric power or electronic signals and exposed machinery and exposed processing equipment and surfaces of particles in storage or transport such as coal, ores, sand and gravel.

Still further, the compositions of the present invention can be used as a deicer and/or anti-icer for pre-harvest fruit and vegetable crops, buds of fruit trees or other vegetation, such as, but not limited to, recreational surfaces such as golf course greens.

DETAILED DESCRIPTION OF THE PREFERRED EMBODIMENTS

The present invention provides novel compositions useful as deicing agents and/or anti-icing agents. The novel compositions of the present invention comprise a by-product from one or more of hydrolysis/esterification reactions and transesterification reactions with triglycerides for the purpose of producing product monoesters for use as biodiesel. Considering these reactions in turn;

Hydrolysis/Esterification

Hydrolysis of triglyceride-containing vegetable and animal fats and oils typically takes place at high temperature and pressure (ca 500 F and 600 psi) in a vertical counter-flow reactor with the fat/oil phase flowing upward and the hot water phase flowing downward. Reactor overheads contain the fatty acid product and the bottoms stream is a water/glycerol stream containing about 12-20% glycerol. The fatty acids so produced then can be reacted with monoalcohols (containing 1-18 carbon atoms) to produce monoesters for use as bio diesel. In this invention it is envisioned that the bottoms product from the hydrolysis reactor, containing about 12-20% glycerol can be employed directly as a component of a deicing or anti-icing formulation. Alternatively, this material may be at least partially concentrated by evaporation.

Transesterification

Transesterification in this instance involves the splitting of the triglyceride ester in the presence of a monohydroxy alcohol (e.g., methanol, ethanol or higher alcohol containing up to 18 carbon atoms) so as to produce monoesters of the fatty acids comprising the original triglycerides. It has been found that esters produced in this fashion can be injected as fuels into diesel engines either pure or blended with fossil diesel. This product has become known as biodiesel. It is also possible to produce the monoesters by direct esterification reaction with the fatty acids separated from the triglycerides by the hydrolysis process described above by reacting these fatty acids with the selected monoalcohol(s).

The present invention employs the glycerol-containing by-product from transesterification reactions, such as biodiesel production, as a valuable component of several deicing and anti-icing formulations. A factor delaying broader use of biodiesel fuels has been the need to find markets for the by-product glycerol to provide income to offset the otherwise high cost of biodiesel fuels. Preferably this market should lie outside the traditional uses for glycerol, and should not require purification to the standards required for the traditional applications. The present inventors unexpectedly have found an economically viable use of triglyceride processing by-products as a de-icing agent and/or anti-icing agent.

There are three basic routes to production of biodiesel employing homogeneous systems:
Base catalyzed transesterification of the oil
Acid catalyzed transesterification of the oil
Conversion of the oil to fatty acids (hydrolysis per above) and subsequent esterification to biodiesel.

The base catalyzed route is the most popular because of the reaction efficiency, mild operating conditions and it requires only simple materials of construction.

In addition to the homogeneous reaction systems, triglycerides can be converted to esters in systems employing heterogeneous catalysts. Such systems are discussed in Stern, et al (U.S. Pat. No. 5,906,946).

Further, as noted earlier, the esters also can be produced by direct esterification of the fatty acids separated from the triglycerides by a hydrolysis reaction with the selected monoalcohols yielding the esters for biodiesel use as well as a water by-product. In this case the glycerol by-product is produced in the hydrolysis stage as discussed above.

In general, the catalyst used for transesterification of the oil to produce biodiesel commercially in homogeneous systems is typically any base, most preferably sodium hydroxide or potassium hydroxide. The catalyst is dissolved in the alcohol using a standard agitator mixer. The alcohol/catalyst mix then is charged into a closed reaction vessel and the oil or fat is added. The system from here is closed totally to the atmosphere to prevent the loss of alcohol. The reaction mix is kept just above the boiling point of the alcohol, around 160° F., to speed up the reaction. Reaction time varies from about 1 to about 8 hours, and some systems recommend that the reaction take place at room temperature. Excess alcohol normally is used to ensure total conversion of the fat or oil to its esters. Care must be taken to monitor the amount of water and free fatty acids in the incoming oil or fat. If the free fatty acid level or water level is too high it may cause problems with soap formation and the separation of the glycerin/glycerol by-product downstream. The general biodiesel reaction is shown below:

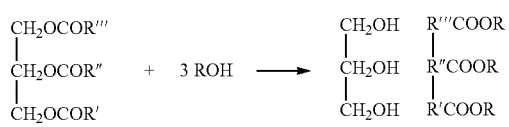

wherein R', R" and R'" independently are the same or different fatty acid chains associated with the oil or fat, typically palmitic, stearic, oleic and linolelic acids for naturally occurring oils and fats. R is any hydrocarbyl compound, generally an alkyl group, such as methyl and/or ethyl.

Once the reaction is complete, two major products exit: a glycerol-containing by-product and a monoester stream (biodiesel). Each has a substantial amount of the excess methanol that was used in the reaction. The reaction catalyst sometimes is neutralized at this step if needed. This neutralization will produce the salt of the base employed—most often sodium chloride. The glycerol phase is much more dense than the biodiesel phase and the two can be gravity separated with glycerol simply drawn off the bottom of the settling vessel. In some cases, a centrifuge may be employed to speed the separation of the two phases.

Once the glycerol and biodiesel phases have been separated, the excess alcohol in each phase is removed via flash evaporation process or by distillation such as in a fractional distillation process conducted at low pressure or under a vacuum. In other systems, the alcohol is removed and the mixture neutralized before the glycerol and esters have been separated. In either case, the alcohol is recovered using distillation equipment and is re-used. In this manner, the glycerol containing by-product comprises a transesterification reactor effluent from which unconverted methanol has been at least partially stripped for recovery and/or recycling.

In many cases the biodiesel phase is water washed to remove traces of glycerol, salt, catalyst and unconverted fatty acids and the separated water from this step generally is mixed with the glycerol phase. This results in a crude glycerol stream comprising glycerol, salt and Miscellaneous Organics Not Glycerol (MONG). In some cases the crude glycerol is recovered by a distillation or evaporation step wherein the remaining liquid has a high glycerol, perhaps 80%, or higher. At atmospheric pressure glycerol boils at 290 C. Operation at such a high temperatures can lead to a dark, discolored product due to degradation or reaction with any remaining fatty acids. For the purposes of the present invention, it may be desirable to remove the alcohol by distillation while still retaining the bulk of the water in the glycerol containing bottoms product. By this procedure, high temperature distillation is avoided that would be the case if the bottoms product were a glycerol concentrate.

The glycerol-containing by-product further may contain salt, catalyst, unreacted fatty acids, unseparated biodiesel and soaps. In accordance with the present invention this glycerol-containing by-product can be used directly as a deicing and/or anti-icing agent of the present invention. In some instances it is desirable to produce an essentially salt free glycerol by-product by distillation. In this case a bottoms stream of high salt content, but still containing substantial glycerol is produced. This material also can be employed in formulations for deicing and anti-icing.

In preferred embodiments, the base catalyst that is employed in the transesterification reaction is neutralized prior to use of the biodiesel by-product as a de-icing and/or anti-icing agent. The base catalyst may be neutralized with any acid, although, generally in commercial reactions with triglycerides to produce products such a biodiesel, soaps and/or fatty acids, the catalyst is neutralized by addition of an inorganic acid such as hydrochloric acid. In the practice of the present invention, the present inventors have found that it is preferred to neutralize the base catalyst with an organic acid, such as, but not limited to acetic and/or lactic acid. Of course, other organic acids such as, but not limited to carbonic, hydroxycarboxylic, carboxylic and/or dicarboxylic acids can be employed as neutralizing agents in accordance with the present invention.

It also is contemplated within the scope of the present invention that prior to employing the biodiesel by-product as the deicing or anti-icing composition, one or more of the catalyst, the unreacted fatty acids, the unseparated biodiesel or other impurities can be removed by conventional separation techniques known to those skilled in the art to provide a substantially pure glycerol-containing by-product stream. A typical procedure is to separate the MONG by reducing the pH of a MONG containing stream.

In the case of heterogeneous systems, such as that taught by Stern, et al., a purer glycerin generally is obtained. To control the possibility of saponification and the resulting production of contaminants in the glycerin product, an esterification reaction with glycerin can be conducted prior to the transesterification reaction essentially to eliminate any free fatty acids in the triglyceride containing feed materials. This can be applied in both the homogeneous and heterogeneous catalyst systems.

In summary, there are several types of glycerin containing by-product streams obtainable from production of monoesters for biodiesel application that can be employed in one or more deicing and/or anti-icing applications. These include, without limitation, the following:

(a) Glycerin-containing streams from homogeneous catalyzed monoester production:
 (i) Crude Glycerin—the by-product from separation of the monoester product from the reactor effluent. In addition to glycerin this stream will normally contain the salt of the basic catalyst used (typically sodium chloride), water added from washing of the monoester product and organic by-products (MONG). Compositions can be about 70-85% glycerin, less than about 20% MONG and about 2-8% salt.
 (ii) Desalted crude glycerin—The crude glycerin can be distilled to produce an essentially salt free product. This material can have about 75-95% glycerin.
 (iii) Purified Glycerin—This stream will be either (1) the distillation overhead if the MONG has been removed prior to distillation, or (2) the Desalted crude Glycerin stream from which the MONMG has been separated. Glycerin content generally will be about 85-95%.
 (iv) USP Glycerin—If the Purified Glycerin has been prepared to a sufficient purity it can be further processed into a product meeting USP specifications. Critical elements are: <Ca 1.7% fatty acids and esters (MONG) as % of glycerin and essentially salt free.
 (v) Salt Bottoms—The bottoms from distillation of the Crude Glycerin will have a variable concentration depending on operation of the distillation process.

(b) Glycerin-containing streams from heterogeneous catalyzed monoester production:
 (i) Separated Glycerin—The glycerin product separated from the product monoesters is reported to contain 98% or more glycerin and contain 0.5% methanol, which needs to be removed for most deicing and/or anti-icing applications. The remaining impurities would be any very small amounts of water introduced with the feedstocks as well as organic compounds such as free fatty acids or saponification products.
 (ii) USP Glycerin—as in the case of glycerin by-product from homogeneous catalysis, the Separated Glycerin can be upgraded to USP specification by common techniques such as acidulation for MONG separation.

(c) Glycerin by-product from hydrolysis of triglycerides to form fatty acids for esterification to monoesters.
 (i) Glycerin/water Product—The glycerin by-product from direct hydrolysis of vegetable and/or animal oils contains about 12-20% glycerin in a well designed system. In some deicing and/or anti-icing applications this material can be used directly to add to other deicing materials such as inorganic salts, or used instead of water in preparing superior non chloride deicing and/or anti-icing formulations such as potassium acetate/glycerin mixtures.
 (ii) Dewatered Glycerin—The Glycerin/water Product can be concentrated up to about 85-95% glycerin by multi-stage evaporation.
 (iii) Purified Glycerin—In turn, Dewatered Glycerin can be concentrated to higher purities by distillation.
 (iv) USP Glycerin—again as in the previous cases, USP Glycerin can be produced.

It also is envisioned that the compositions of the invention can be prepared for use in either a liquid or a solid format. For instance, the compositions can be prepared as a liquid by mixing with water and sprayed or spread on surfaces. Alternatively, it can be prepared in a solid form. Optionally, the solid further may be processed using methods well known in the art such as, for example, pelletizing, prilling, flaking, or macerating to provide the formulation in a final useable solid form. Any of the binders known to those skilled in the art optionally may be present and may either be inert or may be comprised of components that actively help lower the freezing point and/or provide improved traction, for example, cinders, sawdust, sand, gravel, sugars, maltodextrins, naturally occurring minerals such as magnesium chloride, trona and mixtures thereof can be used.

It further is envisioned that the compositions of the present invention also may comprise corrosion inhibitors. Such corrosion inhibitors may include, but are not limited to, inhibitors comprising salts of gluconic acid or inhibitors comprising salts of monocarboxylic acids.

The amount of triglyceride processing by-product deicing or anti-icing composition of the present invention that is required to be effective in the total deicing or anti-icing agent can vary over a considerable range. Preferably the amount varies in the range of from 1 to about 100 weight percent based on the weight of the total composition. For example, we have found that addition of as little as 3% glycerol to a 27% magnesium chloride solution can reduce the eutectic freezing point from −35 C to −46 C. In other cases, the formulation may consist entirely of the by-product material. For example a composition of 32% glycerol, 22% NaCl in water has a freezing point of −32 C which is substantially below the −21 C eutectic of NaCl. In solid formulations, the triglyceride processing by-product deicing and/or anti-icing composition may comprise as much as 100% of the final formulation to be added to the solid carrier material.

It further is contemplated within the scope of the present invention, that in addition to the triglyceride processing by-product, the deicing or anti-icing composition can be combined with an effective freezing point lowering amount of an additive comprising (a) a hydroxyl-containing organic compound selected from the group consisting of hydrocarbyl aldosides; sorbitol and other hydrogenation products of sugars, monosaccharides, maltodextrins and sucrose; maltitol; glycols glycerol; monosaccharides and mixtures thereof, and/or (b) an organic acid salt selected from the group consisting of a carbonic acid salt, a carboxylic acid salt, a hydroxycarboxylic acid salt, a dicarboxylic acid salt and mixtures thereof. The amount of additive generally ranges from about 0.5 to about 95 weight percent based on the weight of the additive and by-product.

Certain of the hydrocarbyl aldosides useful in the practice of the present invention are known to those of ordinary skill in the art such as the di- and polysaccharides. Examples of hydrocarbyl aldosides useful in the practice of the present invention is the glucofuranoside sucrose (table sugar), and maltose and higher polyglucosides.

The hydrocarbyl aldosides also may comprise alkyl aldosides. Alkyl aldosides can be prepared, for example, as described in U.S. Pat. Nos. 4,223,129 and 4,329,449, which are incorporated herein by reference. Typical of the alkyl aldosides useful in the practice of the present invention are alkyl glucosides, alkyl furanosides, alkyl maltosides, alkyl maltotriosides, alkylglucopyranosides, mixtures thereof and the like.

Other hydroxyl-containing compounds useful in the practice of the present invention are sorbitol and other hydrogenation products of sugars, monosaccharides, maltodextrins and sucrose such as maltitol, xylitol and mannitol, or mixtures thereof; glycols such as ethylene glycol, diethylene glycol, dipropylene glycol and propylene glycol; glycerols; and monosaccharides such as glucose, fructose and mixtures thereof. These materials are available commercially and are well known to those of ordinary skill in the art.

The organic salt components useful in the practice of the present invention include the carboxylic acid salts, the hydroxycarboxylic acid salts, dicarboxylic acid salts.

The carboxylic acid salts that are useful in the practice of the present invention are likewise available commercially and are known to those skilled in the art. Carboxylic acid salts preferred for use in the practice of the present invention comprise the sodium or potassium salts of formates, acetates, propionates, butyrates and mixtures thereof. Also preferred are potassium acetate and/or potassium formate.

The hydroxycarboxylic acid salts that are useful in accordance with the present invention are available commercially and are known to those skilled in the art. Preferred hydroxycarboxylic acid salts comprise the sodium and potassium salts of lactic acid such as sodium lactate and potassium lactate, and of gluconic acid such as sodium and potassium gluconate. However, any of the cesium, sodium, potassium, calcium and/or magnesium salts of hydroxycarboxylic acids may be employed such as sodium gluconate.

The dicarboxylic acid salts that are useful in accordance with the present invention are available commercially and are known to those skilled in the art. Preferred dicarboxylic acid salts comprise sodium and potassium salts of oxalates, malonates, succinates, glutarates, adipates, maleates, fumarates and mixtures of any of the foregoing.

Also useful as a deicing component in certain of the compositions of the present invention are the high solubility carbonic acid salts. Preferred carbonate salts for use in the practice of the present invention are potassium carbonate, potassium bicarbonate, sodium carbonate, sodium bicarbonate and cesium carbonate. Potassium carbonate is especially preferred.

Also useful as deicing components in certain compositions of the present invention are the highly soluble salt forms of sodium formate, potassium acetate and sodium lactate. In many applications, the addition of these salts has been found to provide synergistically unexpected reductions in freezing points.

The following table presents some examples of the combination of glycerol with other deicing components:

| Example | 1 | 2 | 3 | 4 | 5 | 6 | 7 | 8 |
|---|---|---|---|---|---|---|---|---|
| Composition, wt % | | | | | | | | |
| Glycerol | 50 | 25 | | 25 | | | 25 | |
| Potassium Carbonate | | 25 | 47 | | | | | |
| Sodium Formate | | | | | | | | |
| Potassium Acetate | | | | 25 | 25 | 50 | | |
| Sodium lactate | | | | | | | 25 | 50 |
| Water | 50 | 50 | 53 | 50 | | 50 | 50 | 50 |
| Freezing point, C. | −23 | −37 | −20 | −41 | −18 | −60 | −39 | −32 |

Comparing examples 1, 2 and 3, it is noteworthy that the freezing point of a 50% mixture of glycerol and potassium carbonate is lower that a 50% solution of glycerol or a 47% solution of potassium carbonate. A comparison of examples 1, 7 and 8 show the same phenomenon with sodium lactate. In the case of potassium acetate (examples 1, 4, 5 and 6), the 25/25 mixture has a freezing point one would expect by a linear interpolation of the freezing point of the components at 50%. In this case, the effect of glycerol substitution is to provide a deicing/anti-icing formulation having a low freezing point, substantially below the freezing point of 25% potassium acetate. This improvement is coupled with the other characteristics provided by glycerol and the other constituents that may be present in a by-product glycerol-containing material. These other characteristics may include, better viscosity and wetting capabilities, and/or corrosion inhibition properties.

In certain instances, where the use of the organic acid components of the present invention causes the pH of the total composition to be too high to meet regulatory or industry specifications, it is contemplated herein to use a buffering agent to lower the pH to acceptable levels. Suitable buffering agents may be selected from any of the known buffering agents. Especially preferred is boric acid. For example in certain highway applications, compositions including potassium carbonate and/or potassium bicarbonate in combination with the triglyceride processing by-product of the present invention, may have a pH above 12 depending on the exact formulation, and most state highway departments prefer deicers having a pH below 12. An effective amount of boric acid or other buffering agent may be added to reduce the pH of the deicing compounds to less than 12, i.e., to from about 11.5 to about 11.8 or lower, to meet the specifications. Alternatively, during the preparation of the carbonate the pH can be adjusted by continued reaction to bicarbonate or separate addition of same.

The present invention still further contemplates combining the triglyceride processing by-product deicing composition with other industrial process streams useful in deicing and/or anti-icing products. For example, the other industrial process streams may be selected from any such streams containing the hydroxyl or organic acid compounds enumerated above including, but not limited to, those selected from the group consisting of a grain stillage, grain steepwaters, wood stillage, corn syrups, products of agricultural or milk fermentation processes, products of sugar extraction processes such a desugared sugar beet molasses and/or desugared sugar cane molasses, hydrogenation products of sugars, monosaccharides, maltodextrins and sucrose and mixtures of any of the foregoing. These industrial streams may be employed directly, or may be treated, such as by alcoholysis to convert the hydroxyl containing compounds to esters, or by reacting convert the organic acids to anionic organic acid salts, such as with a caustic.

Generally the triglyceride processing by-product deicing and/or anti-icing agents useful in the practice of the present invention may be used in solid form, liquid form or liquid form mixed with water.

In addition to (a) the certain hydroxyl-containing organic compounds and (b) the certain organic acid salts, it is contemplated by the present invention that other organic components may be included in the deicing and/or anti-icing compositions of the present invention. Exemplary of such materials are citrate salts such as sodium citrate; amino acids and their salts such as lysine glutamate, sodium pyrrolidone carboxylate and sodium glucoheptonate; lignin components such as lignin sulfonate; boric acid and its salts; sodium gluconate and other gluconic acid salts; and mixtures of any of the foregoing.

In the methods of the present invention, the deicing and/or anti-icing compositions of the present invention are applied, such as by spraying for liquid forms, or spreading for solid forms, onto the surface desired to be treated. In the case of solid forms, the deicing or anti-icing composition can be absorbed or adsorbed onto an inert solid or binder, such as cinders, sand, sawdust, gravel and mixtures thereof; or can be absorbed or adsorbed onto a solid deicing material such as sugars, maltodextrins, inorganic salts (such as sodium chloride, magnesium chloride, trona and mixtures thereof) organic salts (such as sodium and potassium salts of formic acid, acetic acid, lactic acid, calcium magnesium acetate and mixtures thereof); or the solid format can be achieved by processing the composition employing a procedure for converting a liquid to a solid, such as pelletizing, prilling, flaking, macerating and combinations thereof. In the case of deicing, the surface already has ice formed thereon, and the deicing compositions of the present invention melt the ice already formed and are further effective in preventing additional ice formation. In the case of anti-icing, upon learning of a weather forecast that predicts possible dangerous icing conditions, the roads, bridges, airplanes, runways, growing produce or other surfaces can be pretreated with the anti-icing compositions of the present invention in similar manner in order to prevent ice formation on the treated surfaces.

In situations where some inorganic salts such as sodium chloride, magnesium chloride and calcium chloride can be tolerated, the present invention provides an improved method for reducing the amount of salt to be added to achieve an equivalent or better deicing and/or anti-icing effect, and thereby reduce the detriment to the environment. Further, we have found that addition of the glycerol-containing by-products is effective in lowering the effective use of these chlorides into temperature regions substantially below the eutectic points of the simple chloride solutions. For example, we made a mixture of 90% of a crude glycerol stream obtained from soap production, containing glycerol, sodium chloride and some remaining soap and 10% of additional sodium chloride and determined that the resulting liquid did not encounter ice formation until a temperature of −35 C, considerably below the sodium chloride eutectic of −21 C. The addition of salt separated some of the dissolved soap, but a small amount of soap remained providing for good wetting characteristics of the resulting formulation.

Many variations of the present invention will suggest themselves to those skilled in the art in light of the above-detailed description. For example, the triglyceride processing by-product can be combined with any industrial process stream that contains carboxylic acid salts, hydroxycarboxylic acid salts and/or dicarboxylic acid salts in preparing compositions of the present invention. Additionally, a wide variety of glucosides, carbonates, hydrocarbyl aldosides, and a variety of combinations of the components of the present invention may be employed as additives to the triglyceride processing by-product in the compositions of the present invention. All such obvious modifications are within the full-intended scope of the appended claims.

The above-referenced patents, test methods, and publications are hereby incorporated by reference.

The invention claimed is:

1. A method for producing a deicing/anti-icing agent comprising a substantially pure glycerol-containing by-product stream, said by-product stream optionally comprising water, said agent being employed for application to surfaces and for addition to liquids to enable said liquids to function at temperatures below the freezing point of water, and by-product streams comprising salt(s) and miscellaneous organics other than glycerol (MONG), said method comprising:
   i) producing said substantially pure glycerin-containing by-product stream optionally comprising water by;
   a) reacting a triglyceride ester with an alcohol in the presence of a base catalyst to produce a glycerol phase comprising glycerol, catalyst MONG and optionally water and/or unreacted alcohol and a monoester phase that can be processed further in order to be employed as biodiesel;
   b) separating said glycerol phase from said monoester phase;
   c) removing substantially all of the alcohol from the glycerol phase;
   d) neutralizing the glycerol phase with an acid to produce salts from the base catalyst and to separate the MONG; and
   e) removing said salt(s), MONG, and optionally water and/or part of the glycerin from said glycerol phase to produce said substantially pure glycerin-containing by-product stream optionally comprising water, and
   ii) optionally adding to said substantially pure glycerin-containing by-product stream one or more components selected from the group consisting of corrosion inhibitors, hydroxyl containing compounds, organic acid salts, buffers, water and mixtures of any of the foregoing.

2. A method as in claim 1, wherein said liquids enabled to operate at temperatures below the freezing point of water comprise liquids selected from the group consisting of fire extinguisher fluids, heat transfer fluids, engine radiator fluids, oil and gas well drilling fluids, water-based hydraulic fluids, lavatory fluids and mixtures thereof.

3. A method as in claim 1, wherein said surfaces to which said agent is applied are selected from the group consisting of aircraft surfaces, airport runway surfaces, surfaces for vehicular and/or pedestrian use, surfaces of industrial equipment, vegetation surfaces, surfaces of particles selected from the group consisting of coal, ores, sand, gravel, and mixtures thereof.

4. The method of claim 1 wherein said hydroxyl containing compounds are one or more selected from the group consisting of xylitol, sorbitol, maltitol, mannitol, glycols, glycerin and hydrocarbyl aldosides.

5. The method of claim 1 wherein said removing said salt(s), MONG, and optionally water and/or part of the glycerin from said glycerol phase to produce said substantially pure glycerin-containing by-product stream optionally comprising water is accomplished by distillation.

* * * * *